(12) United States Patent
Igami et al.

(10) Patent No.: US 11,189,024 B2
(45) Date of Patent: Nov. 30, 2021

(54) INFORMATION PROCESSING APPARATUS AND INFORMATION PROCESSING METHOD

(71) Applicant: SONY CORPORATION, Tokyo (JP)

(72) Inventors: Toru Igami, Tokyo (JP); Yusuke Nakamura, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 405 days.

(21) Appl. No.: 15/523,012

(22) PCT Filed: Aug. 24, 2015

(86) PCT No.: PCT/JP2015/073751
§ 371 (c)(1),
(2) Date: Apr. 28, 2017

(87) PCT Pub. No.: WO2016/075978
PCT Pub. Date: May 19, 2016

(65) Prior Publication Data
US 2017/0316564 A1 Nov. 2, 2017

(30) Foreign Application Priority Data

Nov. 12, 2014 (JP) .............................. JP2014-229891

(51) Int. Cl.
*G06K 9/46* (2006.01)
*G06T 7/00* (2017.01)
(Continued)

(52) U.S. Cl.
CPC .......... *G06T 7/0012* (2013.01); *A61B 5/0077* (2013.01); *G06K 9/00362* (2013.01);
(Continued)

(58) Field of Classification Search
CPC ................ A61B 5/0022; A61B 5/1118; G06T 2207/30201; G06T 2207/10024;
(Continued)

(56) References Cited

U.S. PATENT DOCUMENTS 8,154,612 B2 * 4/2012 Quan .................. G06K 9/4652
348/222.1
8,175,336 B2 * 5/2012 Kizuki .................... G06T 7/277
382/100
(Continued)

FOREIGN PATENT DOCUMENTS

CN 102741882 A 10/2012
JP 2001-259056 A 9/2001
(Continued)

OTHER PUBLICATIONS

International Search Report and Written Opinion of PCT Application No. PCT/JP2015/073751, dated Nov. 10, 2015, 12 pages of English Translation and 09 pages of ISRWO.

*Primary Examiner* — Matthew C Bella
*Assistant Examiner* — Dennis Rosario
(74) *Attorney, Agent, or Firm* — Chip Law Group

(57) ABSTRACT

Provided is an information processing apparatus including a determination unit that determines at least whether a photographed image is a non-skin region image obtained by photographing a non-skin region, and an output unit that
(Continued)

performs, in the case where the photographed image is determined to be the non-skin region image, a predetermined first output.

17 Claims, 12 Drawing Sheets

(51) Int. Cl.
| | | |
|---|---|---|
| *G06K 9/00* | (2006.01) | |
| *G06T 7/246* | (2017.01) | |
| *G06K 9/62* | (2006.01) | |
| *G06T 7/11* | (2017.01) | |
| *A61B 5/00* | (2006.01) | |

(52) U.S. Cl.
CPC ......... *G06K 9/4642* (2013.01); *G06K 9/6255* (2013.01); *G06T 7/11* (2017.01); *G06T 7/246* (2017.01); *G06T 2207/20021* (2013.01); *G06T 2207/20081* (2013.01); *G06T 2207/30088* (2013.01); *G06T 2207/30168* (2013.01)

(58) Field of Classification Search
CPC ..... G06T 7/90; G06T 7/11; G06T 7/41; G06T 2207/30088; G06T 7/0012; G06T 2207/30196; G06T 5/40; G06T 2207/30004; G06K 9/00234; G06K 9/00228; G06K 9/4652; G06K 9/00375; G06K 2209/05; G06K 9/3233; G06K 9/34; G06K 9/46; G06K 9/00248; G06K 9/00281; G06K 9/00362; G06K 9/00; G06K 9/00221; G06K 9/6253; G06K 9/228; G06K 9/00664; G06K 9/6201; G06K 9/4642; G06K 9/4647; G06F 3/0418; G06F 3/044; G06F 2203/04101; G06F 2203/04104; G06F 3/0416; G06F 3/0488; G06F 3/041; G06F 3/011; G06F 3/0425; G06F 3/0428; H04N 5/23219; H04N 9/643; H04N 1/628; H04N 1/4074; A61M 2230/005; A61M 2230/60; A61M 2230/65; A61K 9/0014

See application file for complete search history.

(56) References Cited

U.S. PATENT DOCUMENTS

| | | | | |
|---|---|---|---|---|
| 8,184,947 B2* | 5/2012 | Murabayashi | ........ | G06F 16/786 386/242 |
| 8,406,482 B1* | 3/2013 | Chien | ................ | G06K 9/4652 382/118 |
| 8,406,519 B1* | 3/2013 | Lim | ....................... | G06T 11/00 382/170 |
| 8,659,622 B2* | 2/2014 | Dhawan | ................ | G06T 3/0012 345/619 |
| 8,879,800 B2* | 11/2014 | Trojanova | ............ | G06K 9/6209 348/673 |
| 8,913,831 B2* | 12/2014 | Bergman | .................. | G06T 7/11 382/173 |
| 9,058,765 B1* | 6/2015 | Mallick | ............... | G06Q 30/0601 |
| 9,313,416 B2* | 4/2016 | Sasaki | ................ | H04N 5/23229 |
| 9,335,826 B2* | 5/2016 | Cheng | ................... | G06F 3/0233 |
| 9,602,685 B2* | 3/2017 | Miyauchi | ............. | G06K 9/6256 |
| 10,438,059 B2* | 10/2019 | Saruta | ................ | G06K 9/00228 |
| 2002/0085219 A1* | 7/2002 | Ramamoorthy | ........ | G06T 15/10 358/1.9 |
| 2009/0016567 A1* | 1/2009 | Aiso | .................... | H04N 1/0044 382/100 |
| 2009/0267893 A1 | 10/2009 | Kato et al. | | |
| 2012/0301032 A1 | 11/2012 | Kawanishi et al. | | |
| 2015/0182191 A1* | 7/2015 | Caluser | ................ | A61B 8/5246 600/440 |

FOREIGN PATENT DOCUMENTS

| | | |
|---|---|---|
| JP | 2004-213127 A | 7/2004 |
| JP | 2007-081682 A | 3/2007 |
| JP | 2008-118635 A | 5/2008 |
| JP | 2009-265809 A | 11/2009 |
| JP | 2010-088863 A | 4/2010 |
| JP | 2011-134034 A | 7/2011 |
| JP | 2012-254221 A | 12/2012 |
| TW | 201329419 A | 7/2013 |
| WO | 2012/073421 A1 | 6/2012 |
| WO | 2013/035847 A1 | 3/2013 |

\* cited by examiner

FIG. 12
IN CONTACT
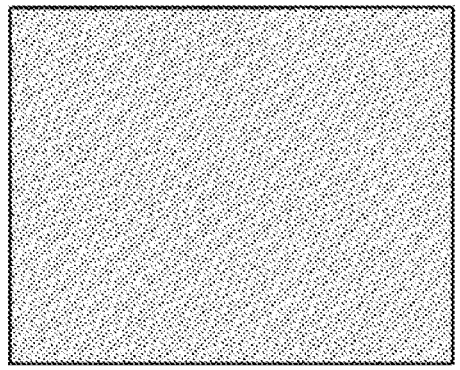
NOT IN CONTACT
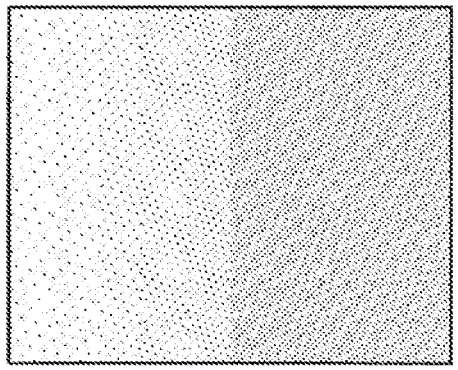

ly photographing an affected part, identifying a position of a camera by which the affected part can be photographed and a composition, and giving feedback on the position of the camera and the composition to a user (for example, see Patent Literature 1).

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2015/073751 filed on Aug. 24, 2015, which claims priority benefit of Japanese Patent Application No. JP 2014-229891 filed in the Japan Patent Office on Nov. 12, 2014. Each of the above-referenced applications is hereby incorporated herein by reference in its entirety.

TECHNICAL FIELD

The present invention relates to an information processing apparatus, an information processing method, and a program.

BACKGROUND ART

There are cases where, in photographing sites such as skin and hair with a camera, a user photographs an image that is unsuitable for a skin analysis or for a diagnosis performed by a specialist. In order to overcome such cases, various technologies have been disclosed. As a first technology, there is disclosed a technology including, for regularly photographing an affected part, identifying a position of a camera by which the affected part can be photographed and a composition, and giving feedback on the position of the camera and the composition to a user (for example, see Patent Literature 1).

As a second technology, there is disclosed a technology including, in the case where a camera shake is detected when a user is photographing sites such as skin and teeth with a camera in his/her hands, outputting an alert display for urging the user to take a necessary action (for example, see Patent Literature 2). In addition, as a third technology, there is given a technology including selecting an appropriate image in terms of a degree of clarity from images that have been buffered through streaming photographing (for example, see Patent Literature 3).

CITATION LIST

Patent Literature

Patent Literature 1: JP 2012-254221A
Patent Literature 2: JP 2008-118635A
Patent Literature 3: JP 2010-88863A

DISCLOSURE OF INVENTION

Technical Problem

However, in the case where a non-skin region is photographed, it is desirable that that the non-skin region has been photographed be output.

Solution to Problem

According to the present disclosure, there is provided an information processing apparatus including: a determination unit configured to determine at least whether a photographed image is a non-skin region image obtained by photographing a non-skin region; and an output unit configured to, in the case where the photographed image is determined to be the non-skin region image, perform a predetermined first output.

According to the present disclosure, there is provided an information processing method, including: determining at least whether a photographed image is a non-skin region image obtained by photographing a non-skin region; and performing, by a processor, a predetermined first output in the case where the photographed image is determined to be the non-skin region image.

According to the present disclosure, there is provided a program for causing a computer to function as an information processing apparatus including: a determination unit configured to determine at least whether a photographed image is a non-skin region image obtained by photographing a non-skin region; and an output unit configured to, in the case where the photographed image is determined to be the non-skin region image, perform a predetermined first output.

Advantageous Effects of Invention

According to the present disclosure described above, in the case where the non-skin region is photographed, it is possible to output that the non-skin region has been photographed. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 12 is a diagram showing an example of a photographed image taken during ultraviolet light irradiation.

MODE(S) FOR CARRYING OUT THE INVENTION

Hereinafter, (a) preferred embodiment(s) of the present disclosure will be described in detail with reference to the appended drawings. In this specification and the appended drawings, structural elements that have substantially the same function and structure are denoted with the same reference signs, and repeated explanation of these structural elements is omitted.

Note that, in this description and the drawings, structural elements that have substantially the same function and structure are sometimes distinguished from each other using different alphabets or numerals after the same reference sign. However, when there is no need in particular to distinguish structural elements that have substantially the same function and structure, the same reference sign alone is attached.

Figure 1:
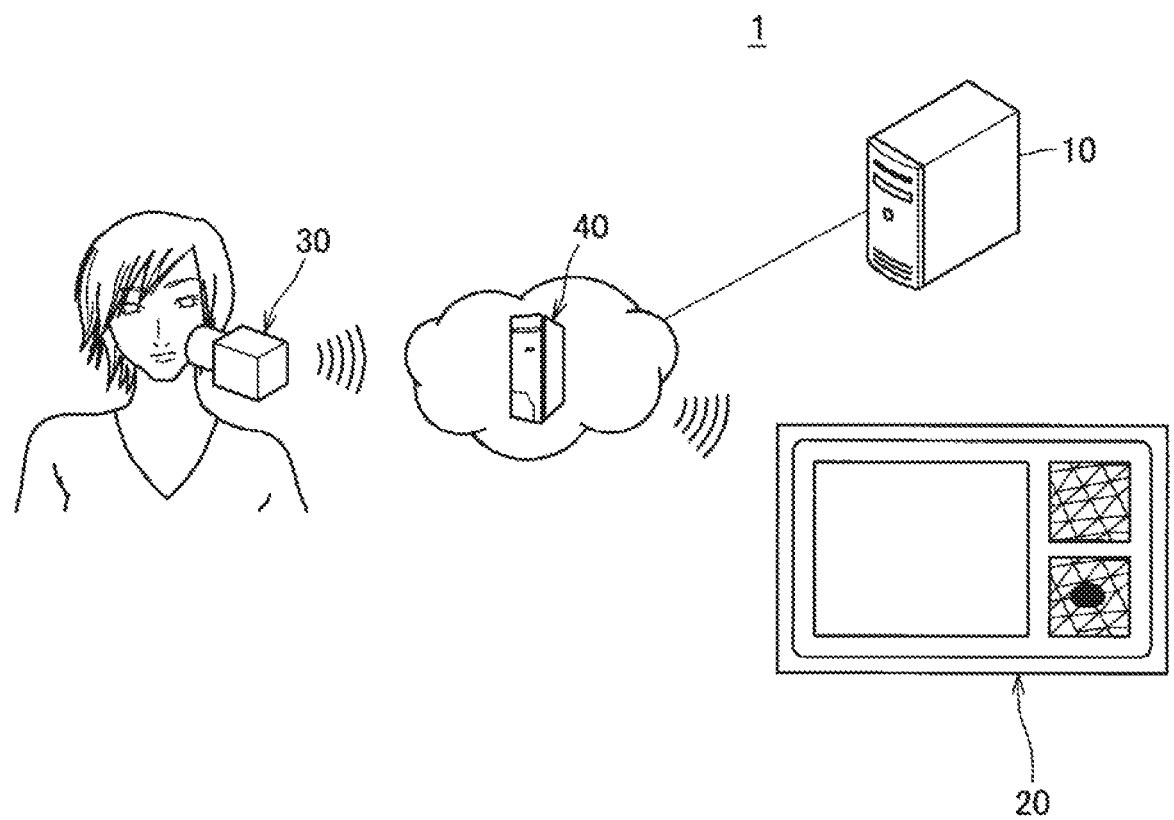
FIG. 1 is a diagram showing a configuration example of a skin analysis system according to an embodiment of the present disclosure.

Note that the description will be given in the following order.
1. Overview of embodiment
2. Functional configuration example of skin analysis system
3. Hardware configuration example of information processing apparatus
4. Conclusion 1. Overview of Embodiment First, an overview of an embodiment of the present disclosure will be described. FIG. 1 is a diagram showing a configuration example of a skin analysis system according to an embodiment of the present disclosure. As shown in FIG. 1, a skin analysis system 1 according to an embodiment of the present disclosure includes a server 10, an information processing terminal 20, and a camera 30. The information processing terminal 20 may be a personal computer (PC), a smartphone, a mobile phone, a tablet PC, a personal digital assistant (PDA), an HMD, or the like. Further, as shown in FIG. 1, the server 10, the information processing terminal 20, and the camera 30 may be mutually communicable with each other via a relay device 40. For example, the relay device 40 may be a Wi-fi (registered trademark) router or the like.

Figure 2:
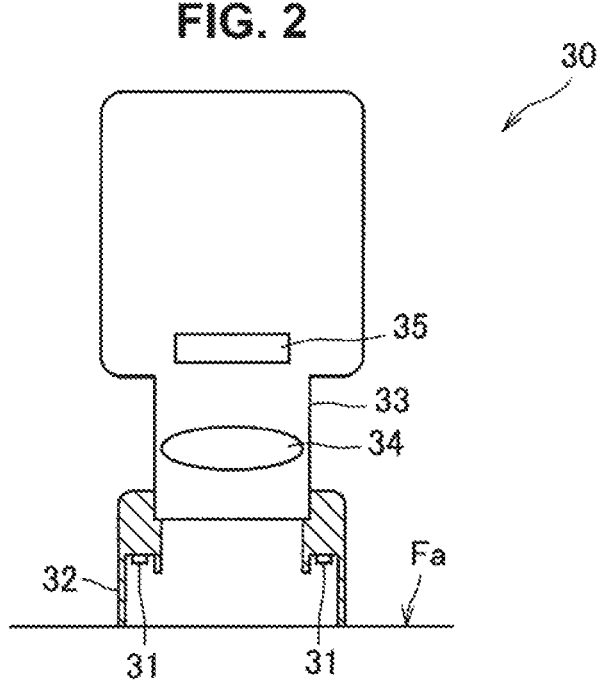
FIG. 2 is a diagram showing a configuration example of a camera.

Here, a configuration example of the camera 30 will be described briefly. FIG. 2 is a diagram showing the configuration example of the camera 30. As shown in FIG. 2, the camera 30 includes an illumination unit 31, a tube 32, a housing 33, a lens 34, and an image sensor 35. The lens 34 and the image sensor 35 are provided inside the housing 33. Further, the illumination unit 31 is provided inside the tube 32.

In the example shown in FIG. 2, the light emitted from the illumination unit 31 reaches a skin surface Fa. Further, the light reflected on the skin surface Fa passes through the lens 34 and reaches the image sensor 35. In this case, in the case where the tube 32 is in contact with the skin surface Fa, the possibility that the light emitted from the illumination unit 31 may leak out of the camera 30 can be reduced, and the possibility that the light which comes inside the camera 30 may reach the image sensor 35 can also be reduced.

A photographed image (still image) taken by the image sensor 35 is transmitted to the server 10, and the server 10 may perform skin analysis processing on the photographed image. Further, a skin analysis result obtained by the skin analysis processing is transmitted to the information processing terminal 20, and the information processing terminal 20 may give feedback of the skin analysis result to a user. Note that, although an example in which the skin analysis processing is performed by the server 10 will be mainly described in the embodiment of the present disclosure, the skin analysis processing may also be performed by the information processing terminal 20 as will be described later.

Figure 3:
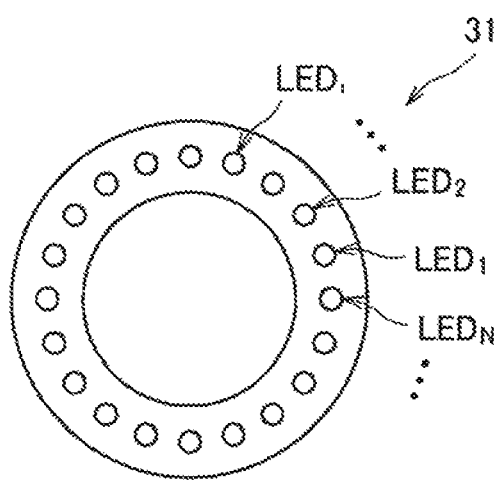
FIG. 3 is a diagram showing a configuration example of an illumination unit.

Subsequently, a configuration example of the illumination unit 31 will be described. FIG. 3 is a diagram showing the configuration example of the illumination unit 31. For example, the illumination unit 31 may include a plurality of illumination light sources. In the example shown in FIG. 3, although the illumination unit 31 includes $LED_1$, $LED_2$, $LED_1$, . . . , $LED_N$ as the plurality of illumination light sources, the type of the illumination light sources is not limited to the organic light emitting diode (LED). In this way, in the case where the illumination unit 31 includes the plurality of illumination light sources, the plurality of illumination light sources can emit light beams which have different photographing conditions (for example, wavelengths and exposure time periods) from each other.

In the embodiment of the present disclosure, assumed is a scene in which the user attempts to photograph a skin region using the camera 30. In such a scene, in the case where the photographed image taken by the camera 30 is inappropriate for the skin analysis processing (or in the case where the photographing situation is inappropriate), the skin analysis system 1 outputs that effect. According to such a configuration, in the case where the photographed image taken by the camera 30 is inappropriate for the skin analysis processing (or in the case where the photographing situation is inappropriate), that effect is output.

Heretofore, the overview of the embodiment of the present disclosure has been described.

2. Functional Configuration Example of Skin Analysis System

Figure 4:
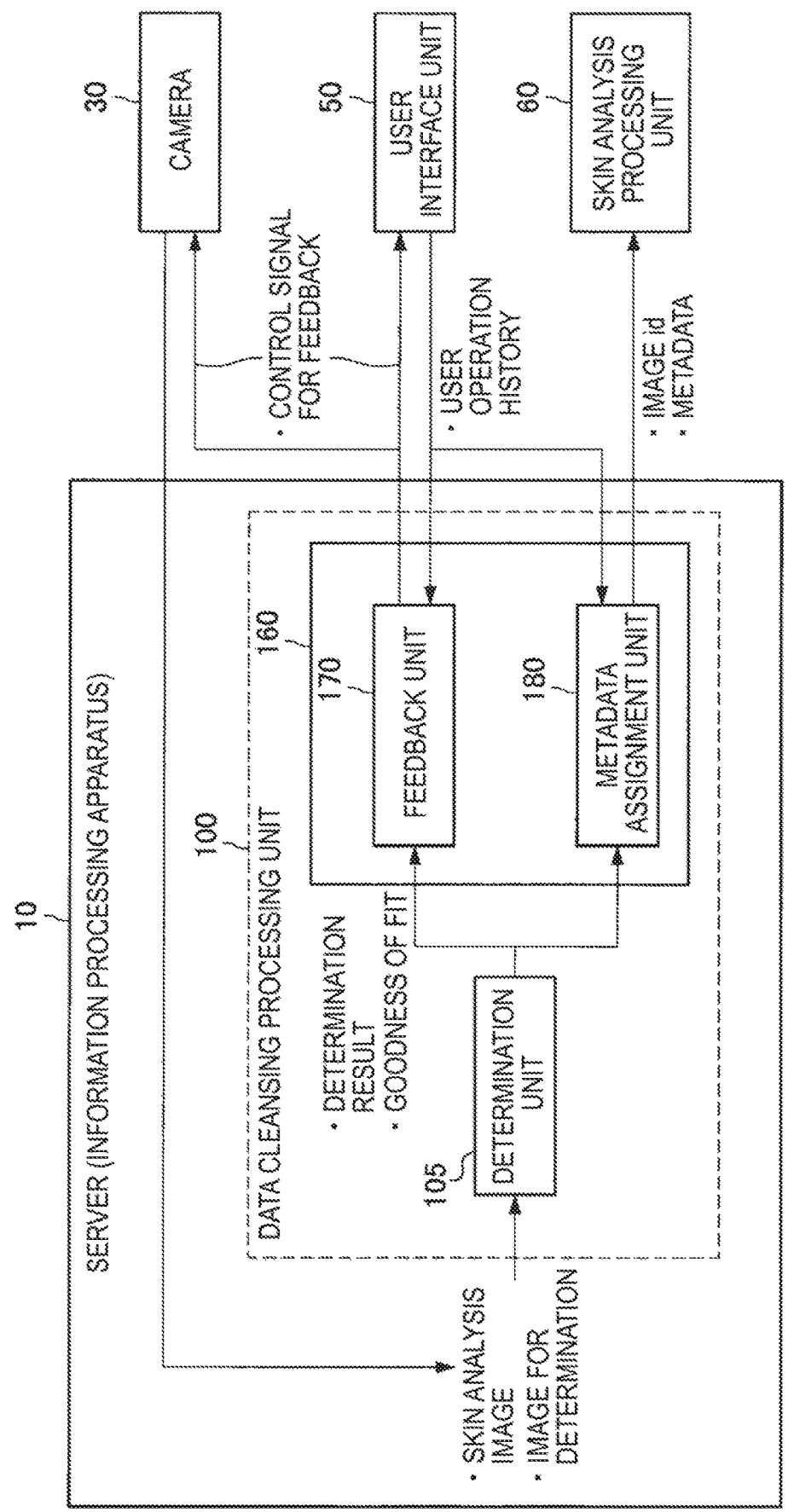
FIG. 4 is a block diagram showing a functional configuration example of a server.

Subsequently, a functional configuration example of the server (information processing apparatus) 10 will be described. FIG. 4 is a block diagram showing the functional configuration example of the server 10. As shown in FIG. 4, the server 10 includes a data cleansing processing unit 100. The data cleansing processing unit 100 includes a determination unit 105 and an output unit 160. The determination unit 105 determines, on the basis of a photographed image input from the camera 30, whether the photographed image input from the camera 30 is inappropriate for the skin analysis processing (or whether the photographing situation is inappropriate). Further, the output unit 160 includes a feedback unit 170 and a metadata assignment unit 180. The details of the output unit 160 will be described later.

Note that, although the description of the present disclosure will describe an example in which the server 10 includes the entire data cleansing processing unit 100, a part of or the entire data cleansing processing unit 100 may be included in another device (for example, the information processing terminal 20 or a dedicated device). Moreover, although the description of the present disclosure will describe an example in which the information processing terminal 20 includes a user interface unit 50, the user interface unit 50 may be included in another device (for example, a dedicated terminal). In addition, although the description of the present disclosure will describe an example in which the server 10 includes a skin analysis processing unit 60, the skin analysis processing unit 60 may be included in another device (for example, information processing terminal 20 or a dedicated device).

Figure 5:
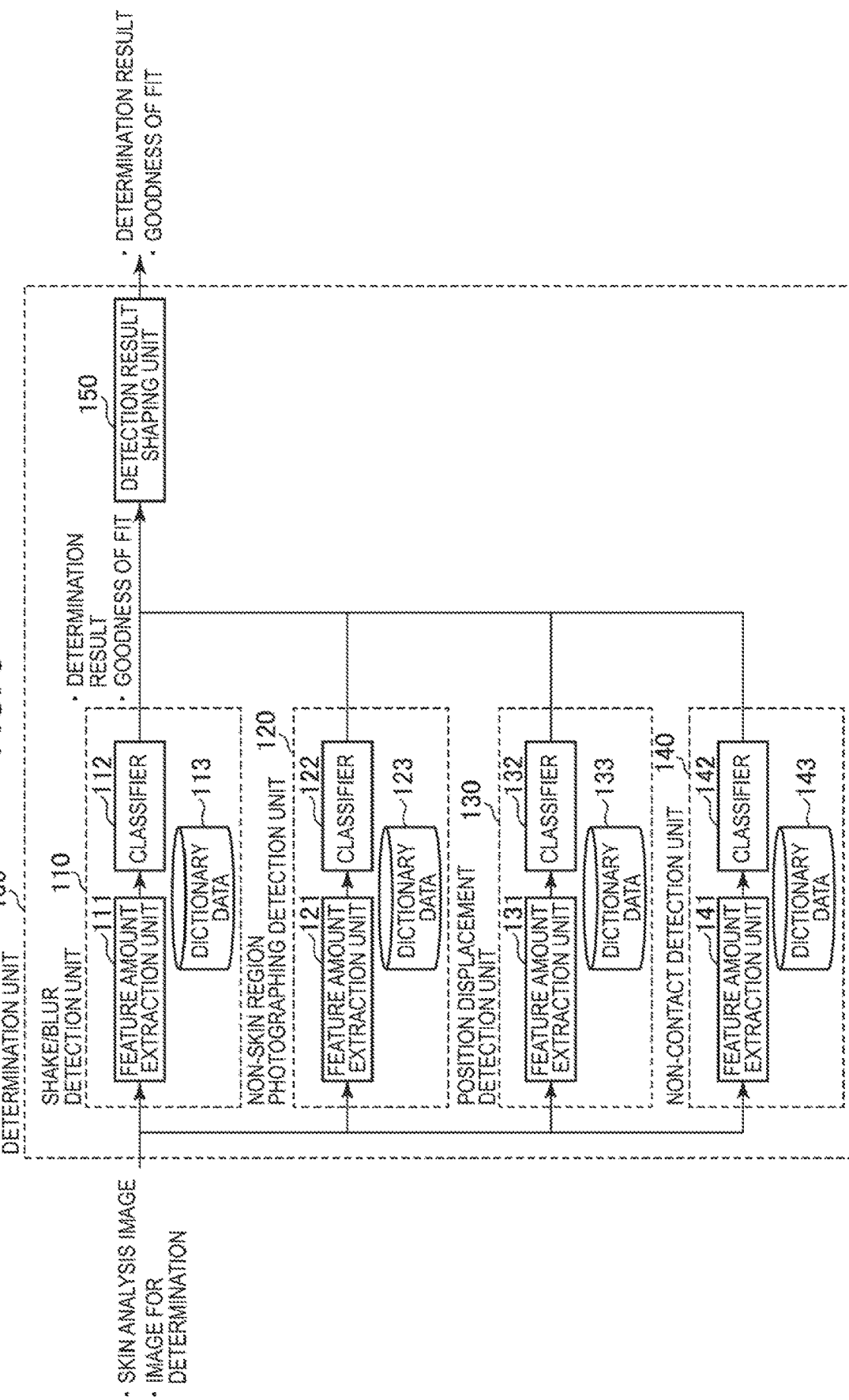
FIG. 5 is a block diagram showing a functional configuration example of a determination unit.

Subsequently, a functional configuration example of the determination unit 105 will be described. FIG. 5 is a block diagram showing the functional configuration example of the determination unit 105. As shown in FIG. 5, the determination unit 105 includes a shake/blur detection unit 110, a non-skin region photographing detection unit 120, a position displacement detection unit 130, a non-contact detection unit 140, and a detection result shaping unit 150. Note that, although the description of the present disclosure will describe an example in which the determination unit 105 includes all of those blocks, the determination unit 105 does not necessarily include some of those blocks.

For example, the determination unit 105 may include any one of the shake/blur detection unit 110, the non-skin region photographing detection unit 120, the position displacement detection unit 130, and the non-contact detection unit 140. Alternatively, the determination unit 105 may include two or three of those blocks in combination. Next, functions of the shake/blur detection unit 110, the non-skin region photographing detection unit 120, the position displacement detection unit 130, and the non-contact detection unit 140 will be described successively.

Figure 6:
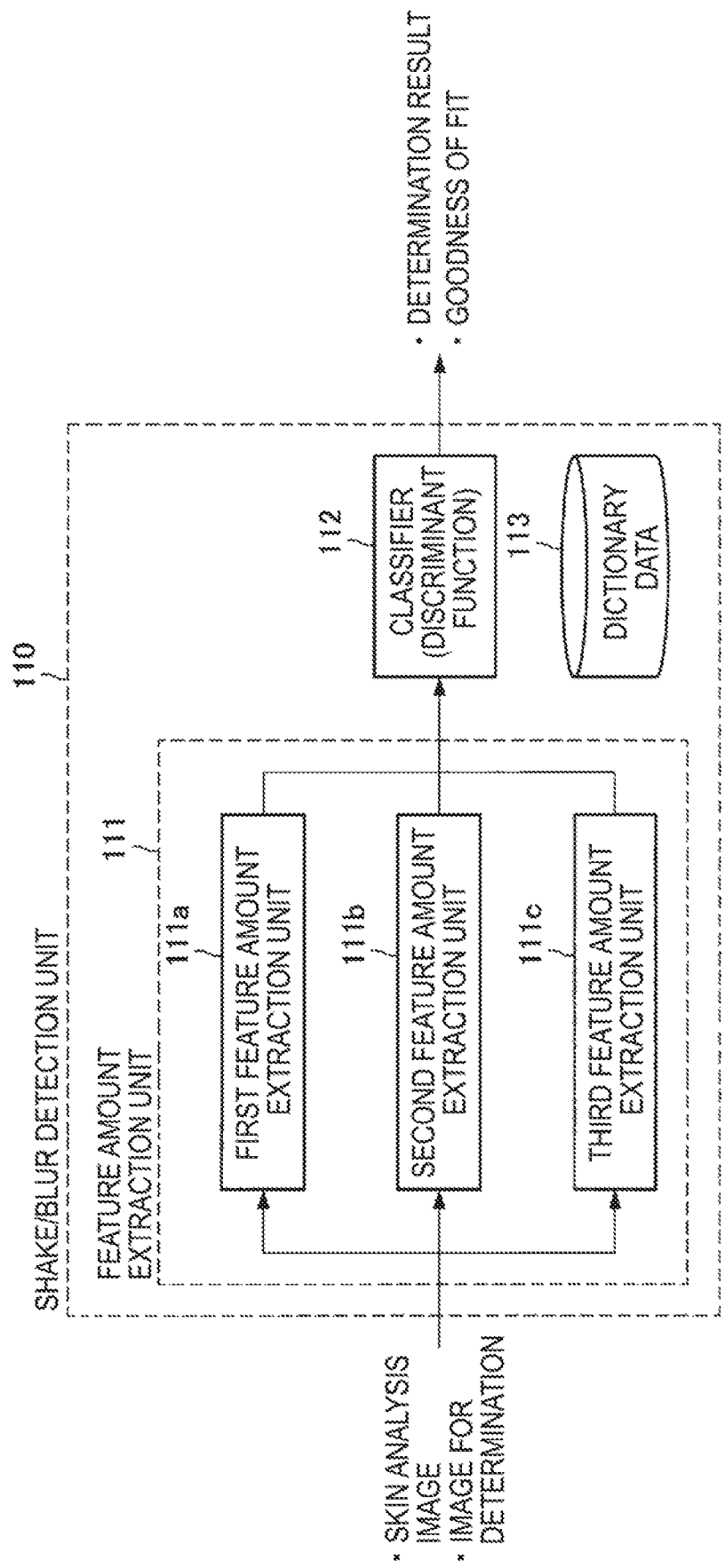
FIG. 6 is a block diagram showing a functional configuration example of a shake/blur detection unit.

FIG. 6 is a block diagram showing a functional configuration example of the shake/blur detection unit 110. Here, in the case where a user photographs skin by the camera 30 that is held in his/her hand, a camera shake may occur. Further, in the case where the pressing of the camera 30 against the skin is insufficient or excessive, defocus may occur. The shake/blur detection unit 110 may determine whether or not a blur or a shake has occurred in the photographed image. As shown in FIG. 6, the shake/blur detection unit 110 includes a feature amount extraction unit 111, a classifier 112, and a dictionary data storage unit 113. The shake/blur detection unit 110 includes a first feature amount extraction unit 111a, a second feature amount extraction unit 111b, and a third feature amount extraction unit 111c.

Here, the first feature amount extraction unit 111a extracts a first feature amount for detecting a blur or a shake in an entire photographed image. To be more specific, the first feature amount extraction unit 111a converts a photographed image taken during white light irradiation into a luminance image. Then, the first feature amount extraction unit 111a calculates a power spectrum of the luminance image. Subsequently, the first feature amount extraction unit 111a integrates amplitudes in each direction of the power spectrum for each frequency band. Next, the first feature amount extraction unit 111a generates, as the first feature amount, a feature vector having integration results for the respective frequency bands as components.

Figure 7:
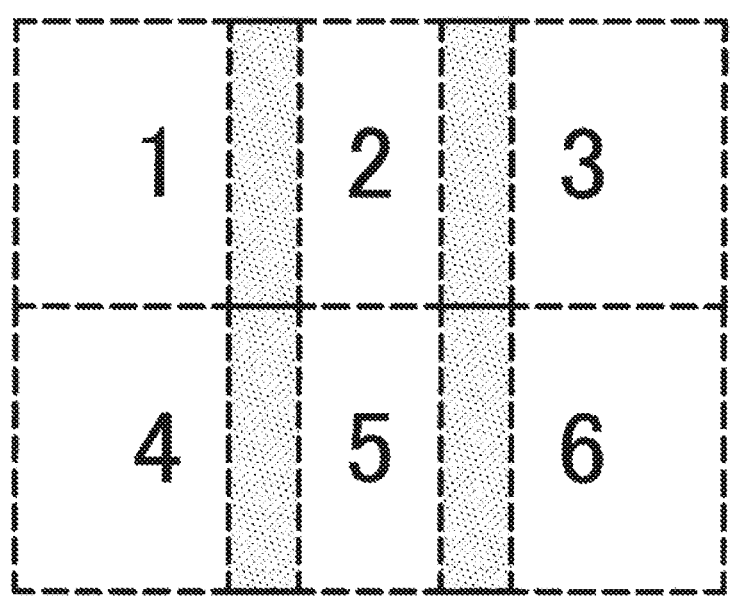
FIG. 7 is a diagram showing an example in which a luminance image is divided into six blocks each having the same sizes.

Further, there is a case where defocus occurs only in one region of the photographed image, which is caused by one side of the camera 30 being detached from the skin and not being in contact with the skin. The second feature amount extraction unit 111b extracts a second feature amount for detecting such defocus. To be more specific, the second feature amount extraction unit 111b converts the photographed image taken during white light irradiation into a luminance image. Then, the second feature amount extraction unit 111b divides the luminance image into six blocks each having the same size. FIG. 7 is a diagram showing an example in which the luminance image is divided into six blocks each having the same size.

Note that, in the case where the camera 30, which performs photographing while being in contact with the skin, is used, there is a characteristic in that the defocus only in one region is likely to occur in any one of the four corners of the photographed image. Using this characteristic, the second feature amount extraction unit 111b may divide the luminance image into blocks of the four corners, each of the blocks having the same size. Alternatively, the second feature amount extraction unit 111b may divide the luminance image into a plurality of blocks each having the same size including the blocks of the four corners.

Then, the second feature amount extraction unit 111b calculates a power spectrum of the luminance image. Subsequently, the second feature amount extraction unit 111b performs a process of integrating amplitudes in each direction of the power spectrum for each frequency band for each block. In this way, feature vectors each having integration results for the respective frequency bands as components are obtained, the number of the feature vectors being the same as the number of the blocks. Next, the second feature amount extraction unit 111b generates, as the second feature amount, a feature vector having as a new component a variance value of components having the same dimension as the feature vectors of the respective blocks.

Further, the third feature amount extraction unit 111c extracts a third feature amount for detecting defocus, for the same object as the extraction of the second feature amount described above. To be more specific, the third feature amount extraction unit 111c converts the photographed image taken during white light irradiation into a luminance image. Then, the third feature amount extraction unit 111c divides the luminance image into six blocks each having the same size (see FIG. 7).

Note that, in the same manner as in the case of extracting the second feature amount described above, the third feature amount extraction unit 111c may also divide the luminance image into blocks of the four corners, each of the blocks having the same size. Alternatively, the third feature amount extraction unit 111c may divide the luminance image into a plurality of blocks each having the same size including the blocks of the four corners. Then, the third feature amount extraction unit 111c calculates the luminance average value for each block. Subsequently, the third feature amount extraction unit 111c generates, as the third feature amount, a feature vector having as a component a difference between the luminance average values of the respective blocks.

The classifier 112 obtains a determination result by determining whether or not a blur or a shake has occurred in the photographed image taken during white light irradiation. To be more specific, the classifier 112 may calculate an evaluation value (hereinafter, also referred to as "goodness of fit") indicating a degree of the blur or a degree of the shake that has occurred in the photographed image, and may determine whether or not the blur or the shake has occurred in the photographed image on the basis of whether the evaluation value is within a predetermined range.

The method of calculating the evaluation value is not particularly limited. For example, let us assume the case where dictionary data is registered in the dictionary data storage unit 113 in advance, the dictionary data being obtained using a learning function on the basis of the first to third feature amounts extracted from an image group in which a shake or a blur has occurred. In this case, a discriminant function may be constructed on the basis of the dictionary data stored in the dictionary data storage unit 113, and the classifier 112 may obtain the evaluation value by inputting the first to third feature amounts extracted by the feature amount extraction unit 111 to the discriminant function.

Note that, in the example shown in FIG. 6, the example has been mainly described in which the first to third feature amounts are extracted as the feature amounts used for creating the dictionary data and the feature amounts extracted from the photographed image. However, all of the first to third feature amounts may not necessarily be used. For example, among the first to third feature amounts, any one of them may be used. Alternatively, among the first to third feature amounts, any two of them may be used in combination, or feature amount(s) other than the first to third feature amounts described here may also be used.

For example, as each of the first and second feature amounts described above, an amplitude for each frequency band of a power spectrum of the luminance image is to be used. However, some sort of information on a frequency of an image (feature amount in which a state of the image in frequency space is described) may be used as a feature amount. For example, a discrete cosine transform (DCT) coefficient at the time of an image being encoded into a joint photographic experts group (JPEG) form by an image signal processor (ISP) included in the camera 30 may be used as a feature amount.

Figure 8:
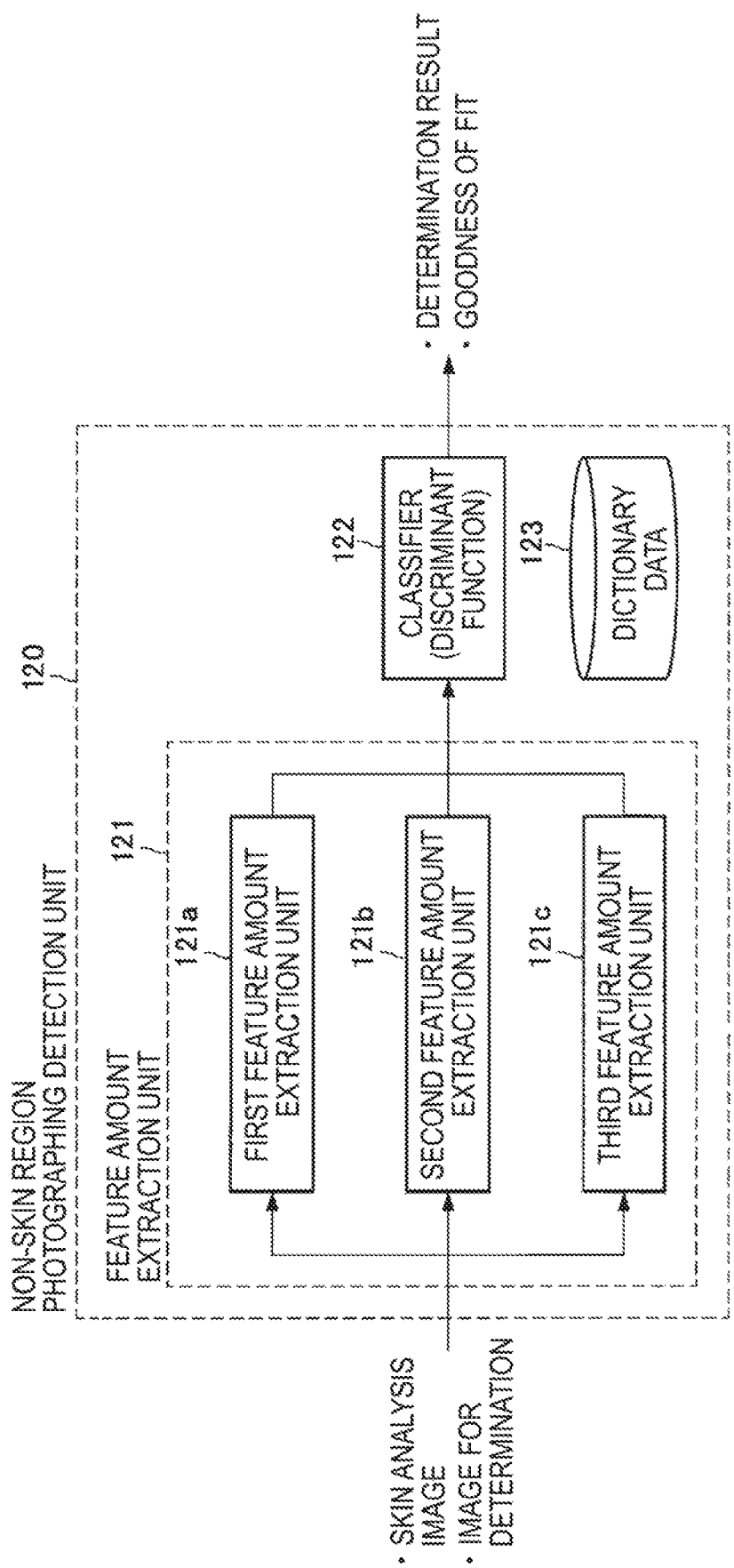
FIG. 8 is a block diagram showing a functional configuration example of a non-skin region photographing detection unit.

FIG. 8 is a block diagram showing a functional configuration example of the non-skin region photographing detection unit 120. Here, when a user attempts to photograph a skin region using the camera 30, there is a case in which a non-skin region is photographed. For example, as the case in which the non-skin region photographed, there is a case in which other than the skin region such as the air, a camera cradle, clothes, or a desk, instead of the skin region, is included in a photographed area. Further, as another case in which the non-skin region is photographed, there is a case in which the skin region included in the photographed area is hidden by hair or a foreign matter such as a patch.

The non-skin region photographing detection unit 120 may determine whether a photographed image is a non-skin region image obtained by photographing a non-skin region. The non-skin region may correspond to a region other than the skin region of the user. As shown in FIG. 8, the non-skin region photographing detection unit 120 includes a feature amount extraction unit 121, a classifier 122, and a dictionary data storage unit 123. The non-skin region photographing detection unit 120 includes a first feature amount extraction unit 121*a*, a second feature amount extraction unit 121*b*, and a third feature amount extraction unit 121*c*.

Here, the first feature amount extraction unit 121*a* extracts a first feature amount. To be more specific, the first feature amount extraction unit 121*a* converts a photographed image taken during white light irradiation into an HSV color space (a color space specifying a color by a combination of a hue, a saturation, and a value). Then, the first feature amount extraction unit 121*a* generates, as the first feature amount, an average value and a variance value of each of the hue and the chroma, and covariance in a hue-chroma space.

Further, the second feature amount extraction unit 121*b* extracts a second feature amount. To be specific, the second feature amount extraction unit 121*b* converts the photographed image taken during white light irradiation into the HSV color space. Then, the first feature amount extraction unit 121*a* generates, as the second feature amount, a map on an appearance frequency in a hue [0, 360]-chroma [0, 1] space on the basis of the HSV color space. The map generated by the first feature amount extraction unit 121*a* may have the hue and the chroma each in units of one.

Further, the third feature amount extraction unit 121*c* extracts a third feature amount. To be more specific, the third feature amount extraction unit 121*c* converts the photographed image taken during white light irradiation into the HSV color space. Then, the third feature amount extraction unit 121*c* generates, as the third feature amount, a histogram of a hue [0, 360].

The classifier 122 obtains a determination result by determining whether or not a blur or a shake has occurred in the photographed image taken during white light irradiation. To be more specific, the classifier 112 may calculate an evaluation value indicating a non-skin region image-likeliness of the photographed image, and may determine whether the photographed image is the non-skin region image on the basis of whether the evaluation value is within a predetermined range.

The method of calculating the evaluation value is not particularly limited. For example, let us assume the case where dictionary data is registered in the dictionary data storage unit 123 in advance, the dictionary data being obtained using a learning function on the basis of the first to third feature amounts extracted from a non-skin region image group. In this case, a discriminant function may be constructed on the basis of the dictionary data stored in the dictionary data storage unit 123, and the classifier 122 may obtain the evaluation value by inputting the first to third feature amounts extracted by the feature amount extraction unit 121 to the discriminant function.

Note that, in the example shown in FIG. 8, the example has been mainly described in which the first to third feature amounts are extracted as the feature amounts used for creating the dictionary data and the feature amounts extracted from the photographed image. However, all of the first to third feature amounts may not necessarily be used. For example, among the first to third feature amounts, any one of them may be used. Alternatively, among the first to third feature amounts, any two of them may be used in combination, or feature amount(s) other than the first to third feature amounts described here may also be used.

For example, in the above description, used as the feature amount is an average value or a variance value of the hue of the photographed image taken during white light irradiation. However, some sort of information on a hue may also be used as a feature amount.

Further, in the case where a proportion of a region in which a difference between pixel values exceeds a threshold is larger than a predetermined proportion, the pixel values corresponding to two photographed images, respectively, the two photographed images being taken during irradiation with light beams having different wavelengths, respectively, the classifier 122 may determine that the photographed image is the non-skin region image. For example, as the light beams having different wavelengths, red light and white light may be used. In this case, the region in which the difference between the pixel values corresponding to the two photographed images exceeds the threshold can be regarded as a region in which hair exists, and the state in which the proportion of the region is larger than the predetermined proportion can be regarded as a state in which a proportion of the region in which hair exists is larger than the predetermined proportion.

Figure 9:
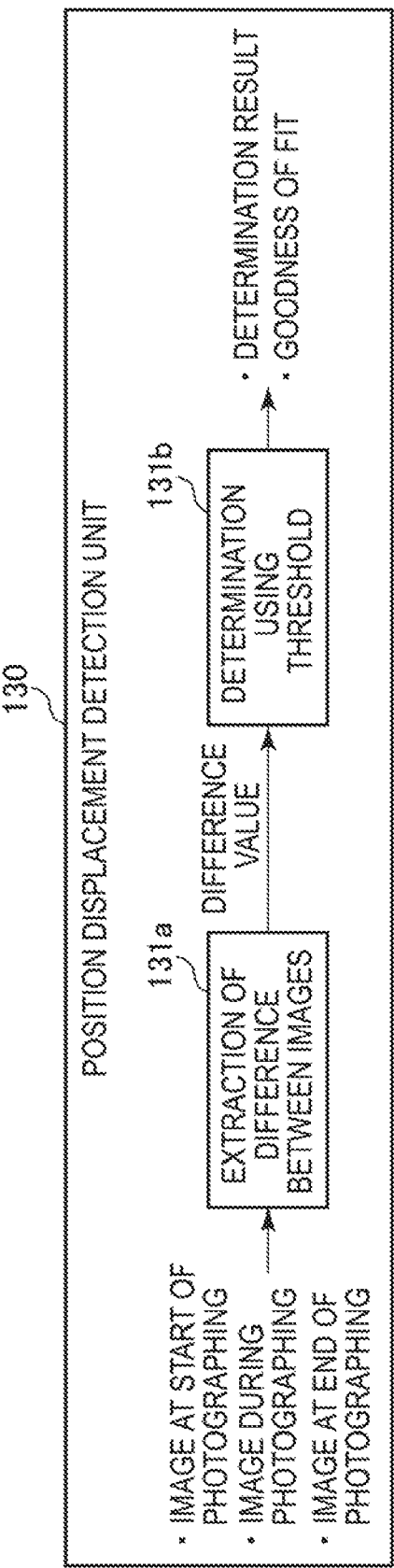
FIG. 9 is a diagram illustrating a function of a position displacement detection unit.
Figure 10:
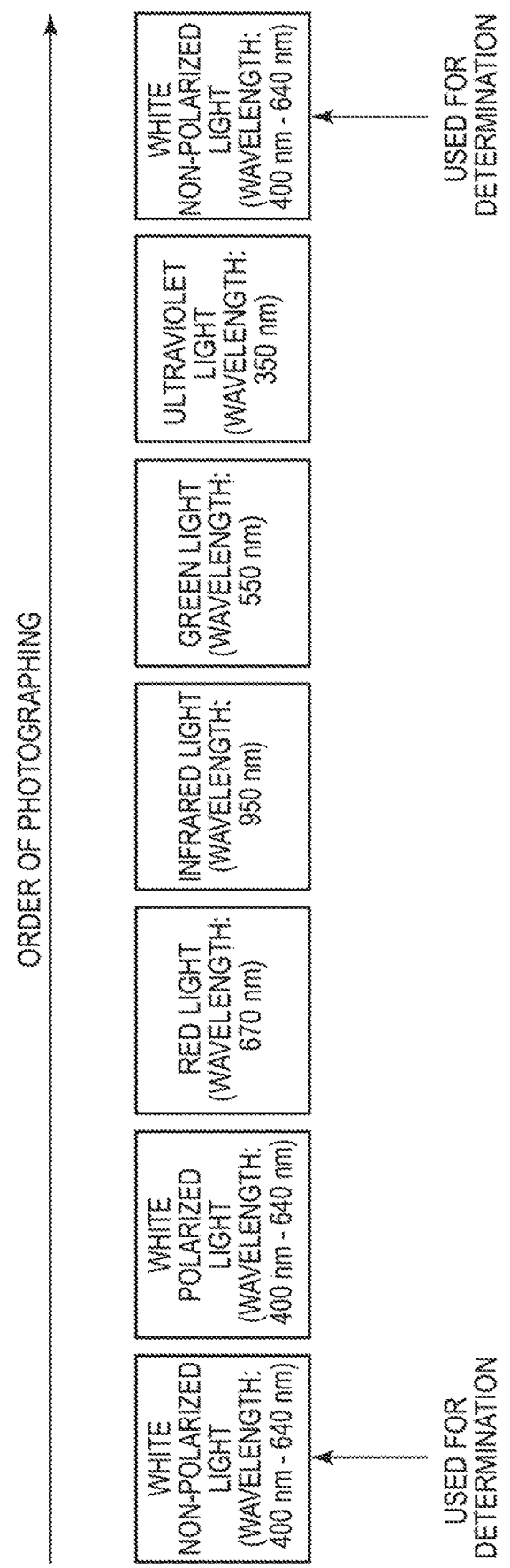
FIG. 10 is a diagram illustrating an example of sequentially photographing a plurality of images.

FIG. 9 is a diagram illustrating a function of the position displacement detection unit 130. Here, it is assumed that the camera 30 sequentially photographs a plurality of images while changing photographing conditions such as spectral conditions and exposure time periods. FIG. 10 is a diagram illustrating an example of sequentially photographing a plurality of images. In this case, with increase in the photographing time period, more likely it is that position displacement occurs which is attributed to a camera shake caused by a user. Further, with increase in the photographing time period, the possibility increases that the user who misunderstands that the photographing has finished may release the camera 30 from a photographing site midway through the photographing.

The position displacement detection unit 130 may determine whether the position displacement of a photographed portion has occurred during the sequential photographing.

As shown in FIG. 9, the position displacement detection unit 130 has, as functions, extraction of difference between images 131a and determination using a threshold 131b. First, a feature amount extraction unit 131 converts two images photographed before and after the plurality of sequentially photographed images (hereinafter, also referred to as "position displacement detection target interval") by the camera 30 into luminance images. Then, the feature amount extraction unit 131 calculates a distance or a degree of similarity between the luminance images.

Subsequently, a classifier 132 determines whether the position displacement has occurred on the basis of the distance or the degree of similarity between the luminance images. To be specific, in the case where the distance between the luminance images exceeds a threshold that is stored in advance as dictionary data in a dictionary data storage unit 133 (in the case where the degree of similarity between the luminance images is less than a threshold), the classifier 132 determines that the position displacement has occurred. On the other hand, in the case where the distance between the luminance images is less than the threshold (in the case where the degree of similarity between the luminance images exceeds the threshold), the classifier 132 determines that the position displacement has not occurred.

The value obtained by subtracting the threshold from the distance (the value obtained by subtracting the degree of similarity from the threshold) may be output as goodness of fit (degree of position displacement). Further, the distance between the luminance images may be the sum of squared errors of pixels corresponding to the respective two luminance images, or may be a distance between luminance histograms generated from the respective two luminance images.

Here, the two images photographed before and after the position displacement detection target interval may be images photographed under the same photographing conditions. FIG. 10 shows the example in which the two images photographed before and after the position displacement detection target interval are images photographed during white non-polarized light irradiation. However, the two images photographed before and after the position displacement detection target interval may be images that are photographed under different photographing conditions (wavelengths of illumination light and the like). In such a case, since it is not necessary to additionally photograph an image for detecting position displacement, the position displacement can be detected more easily.

For example, an image obtained by extracting only a G component of an image photographed during white light irradiation and an image obtained by extracting only a G component of an image photographed during green light irradiation may be used as the two images photographed before and after the position displacement detection target interval. According to such a technique, the classifier 132 can detect the position displacement by the same procedure as described above.

Further, in the case where there is no defocus in both of two images photographed under different photographing conditions, the feature amount extraction unit 131 may describe the two images using local feature amounts, and may calculate a distance or a degree of similarity between the local feature amounts. Then, in the case where the distance between the local feature amounts exceeds a threshold (in the case where the degree of similarity between the local feature amounts is less than a threshold), the classifier 132 may determine that the position displacement has occurred. On the other hand, in the case where the distance between the local feature amounts is less than the threshold (in the case where the degree of similarity between the local feature amounts exceeds the threshold), the classifier 132 may determine that the position displacement has not occurred.

Note that, as the local feature amount, histogram of oriented gradients (HOG), scale invariant feature transform (SIFT), or the like may be used.

Further, the classifier 132 may determine whether the position displacement of the photographed portion has occurred during the sequential photographing using data other than images. For example, the classifier 132 may determine whether the position displacement has occurred on the basis of whether a change in predetermined sensor data exceeds a threshold. For example, the change in sensor data may be an amount of change per unit time of the sensor data.

For example, when a contact sensor is provided on a surface of the camera 30 with which a skin surface Fa comes into contact, in the case where the change in the sensor data obtained by the contact sensor does not exceed a threshold, the classifier 132 can determine that the position of the camera 30 is stable during photographing and the position displacement has not occurred. On the other hand, in the case where the change in the sensor data obtained by the contact sensor exceeds the threshold, the classifier 132 can determine that the position of the camera 30 is unstable during photographing and the position displacement has occurred.

Figure 11:
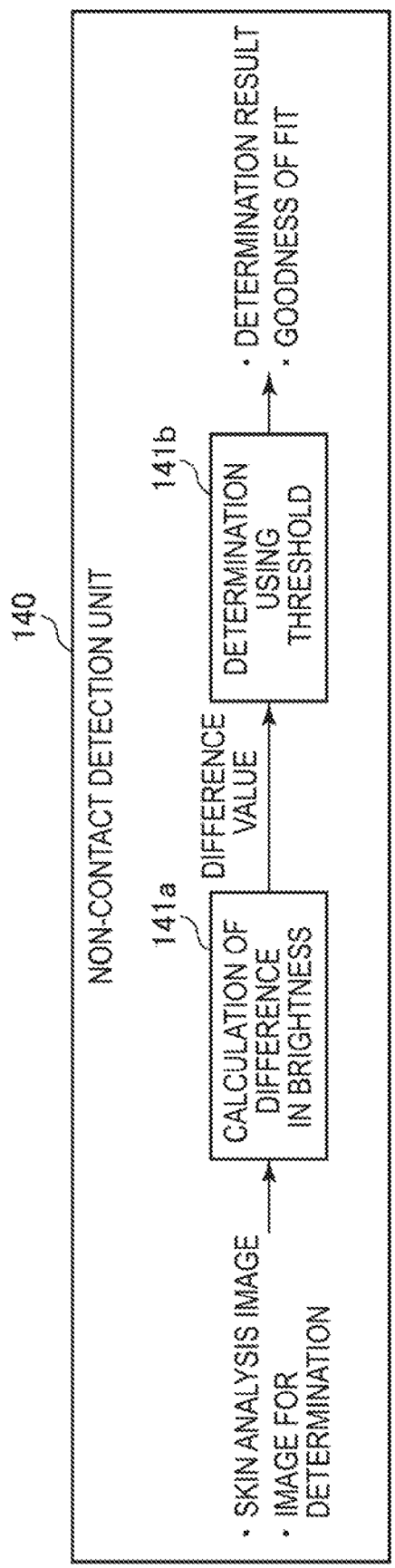
FIG. 11 is a diagram illustrating a function of a non-contact detection unit.

FIG. 11 is a diagram illustrating a function of the non-contact detection unit 140. Here, in the case where an end part of the camera 30 is not in contact with the skin surface Fa, the photographing is performed in the state in which extraneous light enters inside the camera 30. The non-contact detection unit 140 may determine whether the photographed image is taken in a state in which the end part of the camera 30 is not in contact with the skin surface Fa. As shown in FIG. 11, the non-contact detection unit 140 has, as functions, calculation of difference of brightness 141a and determination using a threshold 141b.

First, a feature amount extraction unit 141 converts a photographed image taken during ultraviolet light irradiation or during infrared light irradiation into an HSV color space. Then, the feature amount extraction unit 141 generates a brightness histogram ha of the entire photographed image. A range of the brightness may be [0, 100]. Further, a bin width of the brightness histogram is not limited, and the bin width of the brightness histogram may be "1", for example.

On the other hand, a brightness histogram hb is registered in advance in a dictionary data storage unit 143, the brightness histogram hb being generated on the basis of a contact image group including contact images photographed in a state in which the end part of the camera 30 is in contact with the skin. In the same manner, a brightness histogram hc is registered in advance in the dictionary data storage unit 143, the brightness histogram hc being generated on the basis of a non-contact image group including non-contact images photographed in a state in which the end part of the camera 30 is not in contact with the skin. Accordingly, the feature amount extraction unit 141 calculates a distance d1 between the brightness histogram hb and the brightness histogram ha and a distance d2 between the brightness histogram hc and the brightness histogram ha, using the following formula (1) and formula (2).

$$d1 = \mathrm{dist}(ha, hb) \qquad (1)$$

$$d2 = \mathrm{dist}(ha, hc) \qquad (2)$$

It should be noted that dist(x,y) represents an appropriate distance function with respect to x and y. Subsequently, a classifier 142 determines whether the photographed image is taken in the state in which the end part of the camera 30 is in contact with the skin on the basis of the brightness histogram ha. To be more specific, the classifier 142 determines whether the photographed image is taken in the state in which the end part of the camera 30 is in contact with the skin on the basis of a difference between the distance between the brightness histogram ha and the brightness histogram hc and the distance between the brightness histogram ha and the brightness histogram hb. To be even more specific, the classifier 142 calculates a score s using the following formula (3).

$$s = d1 - d2 \qquad (3)$$

Then, in the case where the score s is less than a threshold, the classifier 142 may determine that the photographed image is taken in the state in which the end part of the camera 30 is not in contact with the skin surface Fa. On the other hand, in the case where the score s is more than or equal to the threshold, the classifier 142 may determine that the photographed image is taken in the state in which the end part of the camera 30 is in contact with the skin surface Fa. The value obtained by subtracting the score s from the threshold may be output as goodness of fit (degree of non-contact).

Note that, commonly used room illumination includes small amounts of light (ultraviolet light) having a wavelength of less than or equal to 400 nm and light having a wavelength of more than or equal to 900 nm compared to the amount of light having a wavelength of 400 nm to 900 nm. On the basis of such a tendency, by using, as the photographed image, a photographed image taken during ultraviolet light irradiation or during infrared light irradiation, the difference between the time at which the camera 30 is in contact with the skin surface Fa and the time at which the camera 30 is not in contact with the skin surface Fa becomes more distinct as described above. FIG. 12 is a diagram showing an example of a photographed image taken during ultraviolet light irradiation.

As shown in FIG. 12, it is grasped that the photographed image taken in the state in which the end part of the camera 30 is in contact with the skin surface Fa during ultraviolet light irradiation has approximately uniform brightness over the entire image. On the other hand, it is grasped that the photographed image taken in the state in which the end part of the camera 30 is not in contact with the skin surface Fa during ultraviolet light irradiation has variation in brightness.

Note that, although FIG. 12 shows the example of the photographed image taken during ultraviolet light irradiation, a red LED which emits light having a wavelength of 650 nm or a blue LED which emits light having a wavelength of 450 nm may be used instead of the LED which emits the ultraviolet light. Also in such a case, whether the photographed image is taken in the state in which the end part of the camera 30 is in contact with the skin surface Fa may be determined with the same technique as described above.

Returning to FIGS. 4 and 5, description will be continued. In the case where it is determined that the photographed image is inappropriate for the skin analysis processing (or the photographing situation is inappropriate), the output unit 160 performs a predetermined output. For example, in the case where the non-skin region photographing detection unit 120 determines that the photographed image is the non-skin region image, the output unit 160 may perform a predetermined first output. Moreover, in the case where the position displacement detection unit 130 determines that the position displacement has occurred, the output unit 160 may perform a predetermined second output.

Further, in the case where it is determined that the photographed image is taken in the state in which the camera 30 is not in contact with the skin surface Fa, the output unit 160 may perform a predetermined third output. Still further, in the case where the shake/blur detection unit 110 determines that a blur or a shake has occurred in the photographed image, the output unit 160 may perform a predetermined fourth output. Such outputs may be performed in any manner. For example, as an example of the outputs, the feedback unit 170 may give predetermined feedback for a user to the user interface unit 50. The predetermined feedback is also not particularly limited.

For example, the predetermined feedback may be an alert display for the information processing terminal 20, may be turning on of an indicator LED of the camera 30, may be activation of a vibrator function of the camera 30, or may be output of an alert sound from a speaker provided to the camera 30 or the information processing terminal 20. Further, the first to fourth outputs may be the same or different from each other. If the first to fourth outputs were different from each other, since different output is performed for each reason for which the photographed image is inappropriate for the skin analysis processing (hereinafter, may also be simply referred to as "reason"), the user can grasp the reason.

For example, the feedback unit 170 may cause the indicator LED of the camera 30 to execute color development correlated with the reason, or may cause the indicator LED of the camera 30 to execute a flashing pattern correlated with the reason. Further, the feedback unit 170 may cause the information processing terminal 20 to display an alert display corresponding to the reason. For example, with increase in the goodness of fit, the feedback unit 170 may increase the amount of information of the alert to be displayed.

Moreover, the feedback unit 170 may perform feedback corresponding to the goodness of fit. In this way, the user can grasp the goodness of fit of the photographed image. For example, the feedback unit 170 may cause the information processing terminal 20 to display an alert display corresponding to the goodness of fit, or may control display or non-display of the alert on the information processing terminal 20 on the basis of the goodness of fit. For example, in the case where the goodness of fit is more than a threshold, the feedback unit 170 may cause the alert to be displayed, and in the case where the goodness of fit is less than the threshold, the feedback unit 170 may cause the alert to be hidden.

Further, the detection result shaping unit 150 may output the determination results output from the shake/blur detection unit 110, the non-skin region photographing detection unit 120, the position displacement detection unit 130, and the non-contact detection unit 140, respectively, to the output unit 160 as they are, or may shape the determination results and then output the shaped determination results to the output unit 160. For example, in the case where it is determined that the photographed image is inappropriate for the skin analysis processing for a plurality of reasons, the detection result shaping unit 150 may perform an output that is different from the first to fourth outputs.

To be more specific, let us assume the case where the shake/blur detection unit 110 determines that a blur or a shake has occurred in the photographed image and the non-contact detection unit 140 determines that the photographed image is taken in the state in which the end part of the camera 30 is not in contact with the skin surface Fa. In such a case, it is presumed that the camera 30 is released from the skin surface Fa, so the feedback unit 170 may output that the camera 30 is released from the skin surface Fa.

Further, let us assume the case where the shake/blur detection unit 110 determines that a blur or a shake has occurred in the photographed image, but the non-contact detection unit 140 determines that the photographed image is taken in the state in which the end part of the camera 30 is in contact with the skin surface Fa. In such a case, it is presumed that the camera 30 is excessively pressed against the skin surface Fa, so the feedback unit 170 may output that the camera 30 is excessively pressed against the skin surface Fa.

Still further, the feedback unit 170 may perform feedback corresponding to a user operation history. For example, the feedback unit 170 may alter the strictness of a threshold (range) used for determining to perform an alert display in accordance with the number of times the user has performed rephotographing. To be more specific, in the case where the number of times the user has performed rephotographing exceeds an upper limit, the range of the goodness of fit for determining to perform the alert display may be narrowed. Accordingly, the troublesomeness given to the user may be suppressed.

Alternatively, the feedback unit 170 may not necessarily give an alert to a user who has a history that indicates the user has rejected an alert display in the past. Accordingly, the troublesomeness given to the user may be suppressed.

Further, in the case where the determination unit 105 determines that the photographed image is appropriate for the skin analysis processing (or the photographing situation is appropriate) but the user inputs that the photographed image is inappropriate for the skin analysis processing (or the photographing situation is inappropriate), the feedback unit 170 may broaden the range of the goodness of fit for determining to perform the alert display.

On the other hand, in the case where the determination unit 105 determines that the photographed image is inappropriate for the skin analysis processing (or the photographing situation is inappropriate) but the user inputs that the photographed image is appropriate for the skin analysis processing (or the photographing situation is appropriate), the feedback unit 170 may narrow the range of the goodness of fit for determining to perform the alert display.

The metadata assignment unit 180 may output, as metadata, that the photographed image is inappropriate for the skin analysis processing (or the photographing situation is inappropriate) to the skin analysis processing unit 60 that analyzes the photographed image, for example. For example, the metadata assignment unit 180 may output, as metadata, a value indicating whether the photographed image is inappropriate for the skin analysis processing (or a value indicating whether the photographing situation is inappropriate) to the skin analysis processing unit 60, for each reason. Alternatively, the metadata assignment unit 180 may output, as metadata, the goodness of fit for each reason.

The skin analysis processing unit 60 can control a parameter used for the skin analysis processing on the basis of the metadata. As an example, in the case where that it is determined that a blur or a shake has occurred in the photographed image is input as the metadata, the skin analysis processing unit 60 may increase a score for judging smoothness of the skin.

Alternatively, the skin analysis processing unit 60 can control a weighting to data at a time of statistical data calculation on the basis of the metadata. For example, the skin analysis processing unit 60 may not necessarily use the photographed image which has been determined as inappropriate for the skin analysis processing for the statistical data calculation. Further, the skin analysis processing unit 60 may decrease the weighting of the photographed image which has been determined as inappropriate for the skin analysis processing.

Moreover, in the case where the user determines whether to use the photographed image for the skin analysis and inputs an operation in accordance with the determined result, the metadata assignment unit 180 may associate the user operation history with the image. Such a user operation history may also be used as labelling data used for creating dictionary data for detecting an image inappropriate for the skin analysis.

Note that the metadata output from the metadata assignment unit 180 may be shaped into a form that can be handled in the skin analysis processing unit 60 by the metadata assignment unit 180. Note that, as shown in FIG. 4, the metadata assignment unit 180 may output an image id together with the metadata to the skin analysis processing unit 60. Alternatively, the metadata assignment unit 180 may output an image for skin analysis together with the metadata to the skin analysis processing unit 60.

Heretofore, the functional configuration example of the skin analysis system 1 according to an embodiment of the present disclosure has been described.

3. Hardware Configuration Example of Information Processing Apparatus

Figure 13:
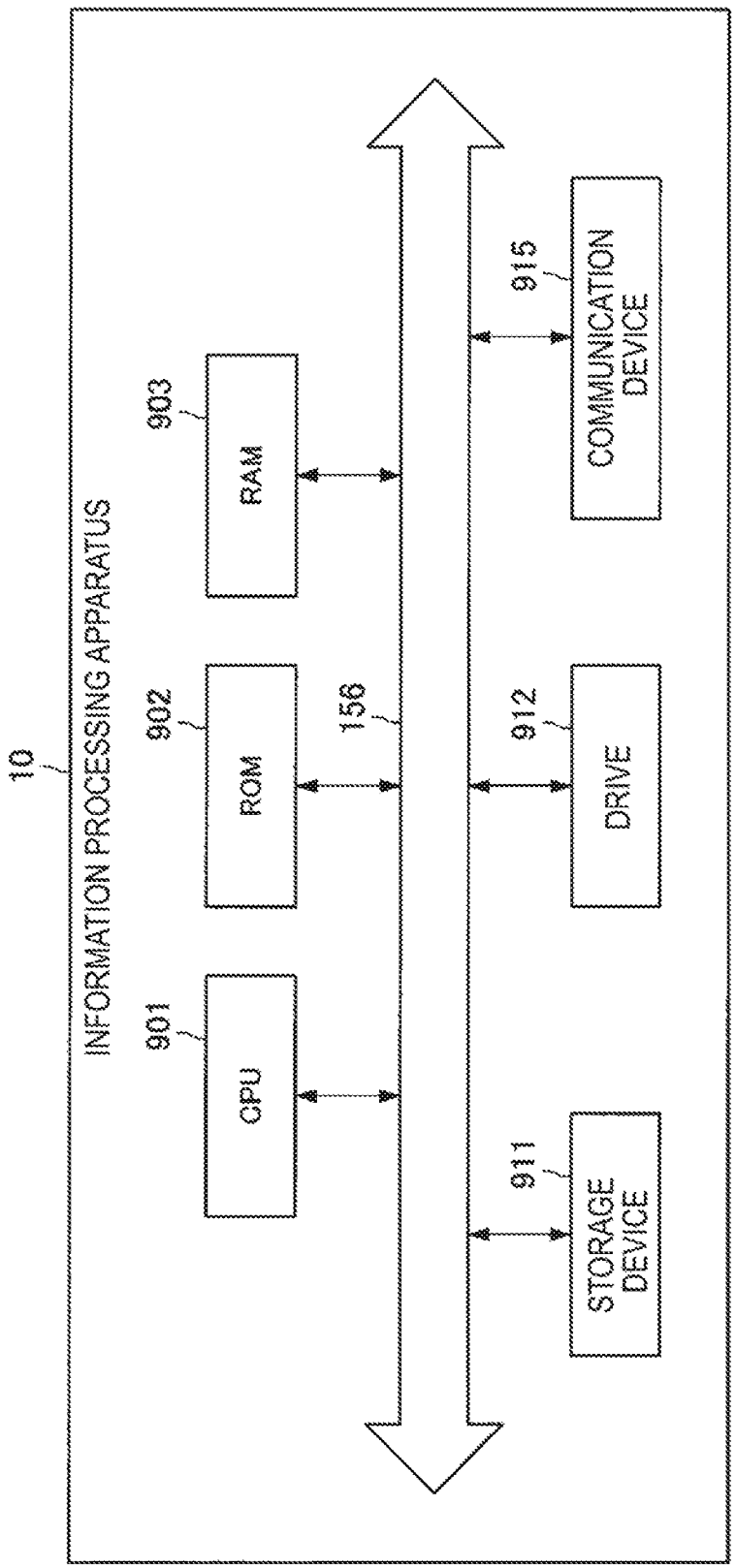
FIG. 13 is a diagram showing a hardware configuration example of an information processing apparatus according to the embodiment.

Subsequently, a hardware configuration example of the information processing apparatus 10 according to an embodiment of the present disclosure will be described. FIG. 13 is a diagram showing the hardware configuration example of the information processing apparatus 10 according to an embodiment of the present disclosure. However, the hardware configuration example shown in FIG. 13 merely shows an example of the hardware configuration of the information processing apparatus 10. Accordingly, the hardware configuration of the information processing apparatus 10 is not limited to the example shown in FIG. 13.

As shown in FIG. 13, the information processing apparatus 10 includes a central processing unit (CPU) 901, read only memory (ROM) 902, random access memory (RAM) 903, a storage device 911, a drive 912, and a communication device 915.

The CPU 901 functions as an arithmetic processing device and a control device, and controls entire operation of the information processing apparatus 10 in accordance with various programs. Further, the CPU 901 may be a microprocessor. The ROM 902 stores a program, a calculation parameter, and the like used by the CPU 901. The RAM 903 temporarily stores a program used in execution of the CPU 901, a parameter varying as appropriate during the execution, and the like. They are connected with each other via the host bus 156 configured from a CPU bus or the like.

The storage device 911 is an example of a storage unit of the information processing apparatus 10, and is a device for storing data. The storage device 911 may include, for example, a storage medium, a recording device for recording data in the storage medium, a reading device for reading out the data from the storage medium, and a deletion device for deleting the data recorded in the storage medium. The storage device 911 stores a program executed by the CPU 901 and various data.

The drive 912 is a reader/writer for the storage medium and is built in or externally attached to the information processing apparatus 10. The drive 912 reads out information recorded in a removable storage medium which is mounted thereto, such as a magnetic disk, an optical disc, a magneto-optical disk, or semiconductor memory, and outputs the information to the RAM 903. Further, the drive 912 can also write the information in the removable storage medium.

The communication device 915 communicates via a network (or directly) with an external device. The communication device 915 may be an interface for radio communication, and may include a communication antenna, a radio frequency (RF) circuit, and a base band processor, for example. Specific examples of the interface for radio communication include communication units such as modems that support communication schemes such as code division multiple access (CDMA), wideband code division multiple access (W-CDMA), long term evolution (LTE), and wireless fidelity (Wi-fi) (registered trademark).

Further, the communication device 915 may be an interface for wired communication, and may include a connection terminal, a transmission line, and other circuits for communication processing, for example. The CPU 901 and the communication device 915 may be configured on one chip, or may be provided as separate devices. Although not shown in FIG. 13, the information processing apparatus 10 may be driven by power supplied from a power source such as a rechargeable battery, for example, and the power source may be attachable to and detachable from the information processing apparatus 10.

Heretofore, the hardware configuration example of the information processing apparatus 10 according to an embodiment of the present disclosure has been described.

4. Conclusion

As described above, according to an embodiment of the present disclosure, there is provided the information processing apparatus 10 including the determination unit 105 configured to determine at least whether a photographed image is a non-skin region image obtained by photographing a non-skin region, and the output unit 160 configured to, in the case where the photographed image is determined to be the non-skin region image, perform a predetermined first output. According to such a configuration, in the case where the non-skin region is photographed in the scene in which the user attempts to photograph a skin region using the camera 30, that the non-skin region has been photographed may be output.

Hereinafter, differences between the technologies written in Patent Literatures and the technology according to an embodiment of the present disclosure will be described in detail. First, as the first technology, there is disclosed a technology, for regularly photographing an affected part, including identifying a position of a camera by which the affected part can be photographed and a composition, and giving feedback on the position of the camera and the composition to a user (for example, see Patent Literature 1). However, the technology written in Patent Literature 1 is used for determining whether the same affected part has been photographed, and it is not possible to detect an image including a shake or a blur, a non-skin region photographed image, position displacement, or the like, and to give feedback of the detection results to the user.

As the second technology, there is disclosed a technology including, in the case where a camera shake is detected when a user is photographing sites such as skin and teeth with a camera in his/her hands, outputting an alert display for urging the user to take a necessary action (for example, see Patent Literature 2). However, it is not possible for the technology written in Patent Literature 2 to detect a non-skin region photographed image, position displacement, non-contact of the camera 30 to the skin, or the like. In addition it is not possible for the technology written in Patent Literature 2 to give a feedback to the user taking into account inappropriateness of the photographed image.

Moreover, as the third technology, there is given a technology including selecting an appropriate image in terms of a degree of clarity from images that have been buffered through streaming photographing (for example, see Patent Literature 3). However, the technology written in Patent Literature 3 can only acquire an image that has been photographed under the same photographing condition as the photographing condition of the streaming photographing. Accordingly, Patent Literature 3 cannot be applied to the case where sequential photographing is attempted while altering wavelengths of light, exposure time periods, and the like. On the other hand, according to an embodiment of the present disclosure, an image photographed under a photographing condition different from the photographing condition of the streaming photographing can be used for a skin analysis.

Further, even in the case where an image that has been photographed under the same photographing condition as the photographing condition of the streaming photographing is to be acquired, the technology written in Patent Literature 3 may be restricted in a part related to a data size such as resolution of an image, due to restrictions on memory I/O, a transfer rate, and data throughput for determining a degree of clarity during the streaming photographing.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, it is also possible to create a program for causing hardware such as a CPU, ROM, and RAM, which are built in a computer, to exhibit substantially the same functions as the respective functions of the information processing apparatus 10 described above. Further, there is also provided a computer-readable recording medium having the program recorded thereon.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including:

a determination unit configured to determine at least whether a photographed image is a non-skin region image obtained by photographing a non-skin region; and an output unit configured to, in the case where the photographed image is determined to be the non-skin region image, perform a predetermined first output.

(2)

The information processing apparatus according to (1), wherein, in the case where the photographed image is determined to be the non-skin region image, the output unit includes a feedback unit configured to give predetermined feedback to a user.

(3)

The information processing apparatus according to (1), wherein, in the case where the photographed image is determined to be the non-skin region image, the output unit includes a metadata assignment unit configured to output that the photographed image is the non-skin region image to a skin analysis processing unit configured to analyze the photographed image.

(4)

The information processing apparatus according to any one of (1) to (3), wherein the determination unit calculates an evaluation value indicating a non-skin region image-likeliness of the photographed image, and determines whether the photographed image is the non-skin region image on the basis of whether the evaluation value is within a predetermined range.

(5)

The information processing apparatus according to (4), wherein the determination unit obtains the evaluation value by inputting at least information on a hue obtained from the photographed image to a discriminant function that has been generated in advance.

(6)

The information processing apparatus according to any one of (1) to (3), wherein the determination unit determines that the photographed image is the non-skin region image in the case where a proportion of a region in which a difference between pixel values exceeds a threshold is larger than a predetermined proportion, the pixel values corresponding to two photographed images, respectively, the two photographed images being taken during irradiation with light beams having different wavelengths, respectively.

(7)

The information processing apparatus according to any one of (1) to (6), wherein the determination unit determines whether position displacement of a photographed portion has occurred during sequential photographing, and the output unit performs, in the case where it is determined that the position displacement has occurred, a predetermined second output.

(8)

The information processing apparatus according to (7), wherein the determination unit determines whether the position displacement has occurred on the basis of a distance or a degree of similarity between luminance images of respective two images, the two images being photographed before and after a plurality of sequentially photographed images.

(9)

The information processing apparatus according to (7), wherein the determination unit determines whether the position displacement has occurred on the basis of whether a change in predetermined sensor data exceeds a threshold.

(10)

The information processing apparatus according to any one of (1) to (9), wherein the determination unit further determines whether the photographed image is taken in a state in which a camera is not in contact with a skin, and the output unit performs, in the case where it is determined that the photographed image is taken in the state in which the camera is not in contact with the skin, a predetermined third output.

(11)

The information processing apparatus according to (10), wherein the determination unit determines whether the photographed image is taken in the state in which the camera is not in contact with the skin on the basis of a brightness histogram obtained from the photographed image.

(12)

The information processing apparatus according to (11), wherein the determination unit determines whether the photographed image is taken in the state in which the camera is not in contact with the skin on the basis of a difference between a distance between a brightness histogram obtained from the photographed image and a brightness histogram at a time in which the camera is not in contact with the skin that is registered in advance and a distance between the brightness histogram obtained from the photographed image and a brightness histogram at a time in which the camera is in contact with the skin.

(13)

The information processing apparatus according to any one of (1) to (12), wherein the determination unit further determines whether or not a blur or a shake has occurred in the photographed image, and the output unit performs, in the case where it is determined that the blur or the shake has occurred in the photographed image, a predetermined fourth output.

(14)

The information processing apparatus according to (13), wherein the determination unit calculates an evaluation value indicating a degree of the blur or a degree of the shake that has occurred in the photographed image, and determines whether or not the blur or the shake has occurred in the photographed image on the basis of whether the evaluation value is within a predetermined range.

(15)

The information processing apparatus according to (14), wherein the determination unit obtains the evaluation value by inputting at least information on a frequency obtained from the photographed image to a discriminant function that has been generated in advance.

(16)

The information processing apparatus according to (14), wherein the determination unit obtains the evaluation value by inputting at least a difference between luminance average values of respective blocks obtained from the photographed image to a discriminant function that has been generated in advance.

(17)

The information processing apparatus according to (2), wherein the determination unit calculates an evaluation value indicating a non-skin region image-likeliness of the photographed image, and determines whether the photographed image is the non-skin region image on the basis of whether the evaluation value is within a predetermined range, and the feedback unit performs feedback corresponding to the evaluation value.

(18)

The information processing apparatus according to (3), wherein the determination unit calculates an evaluation value indicating a non-skin region image-likeliness of the photographed image, and determines whether the photographed image is the non-skin region image on the basis of whether the evaluation value is within a predetermined range, and the metadata assignment unit outputs the evaluation value or data corresponding to the evaluation value to the skin analysis processing unit.

(19)

An information processing method, including:

determining at least whether a photographed image is a non-skin region image obtained by photographing a non-skin region; and performing, by a processor, a predetermined first output in the case where the photographed image is determined to be the non-skin region image.

(20)

A program for causing a computer to function as an information processing apparatus including:

a determination unit configured to determine at least whether a photographed image is a non-skin region image obtained by photographing a non-skin region; and an output unit configured to, in the case where the photographed image is determined to be the non-skin region image, perform a predetermined first output.

REFERENCE SIGNS LIST

1 skin analysis system
10 server (information processing apparatus)
20 information processing terminal
30 camera
31 illumination unit
32 tube
33 housing
34 lens
35 image sensor
40 relay device
50 user interface unit
60 skin analysis processing unit
100 data cleansing processing unit
105 determination unit
110 shake/blur detection unit
111 feature amount extraction unit
111a first feature amount extraction unit
111b second feature amount extraction unit
111c third feature amount extraction unit
112 classifier
113 dictionary data storage unit
120 non-skin region photographing detection unit
121 feature amount extraction unit
121a first feature amount extraction unit
121b second feature amount extraction unit
121c third feature amount extraction unit
122 classifier
123 dictionary data storage unit
130 position displacement detection unit
131 feature amount extraction unit
132 classifier
133 dictionary data storage unit
140 non-contact detection unit
141 feature amount extraction unit
143 dictionary data storage unit
142 classifier
150 detection result shaping unit
160 output unit
170 feedback unit
180 metadata assignment unit

The invention claimed is:

1. An information processing apparatus, comprising:
a memory configured to register dictionary data, wherein the registered dictionary data is obtained based on a learning function and a hue of a non-skin region image group; and
a central processing unit (CPU) configured to:
calculate a first evaluation value based on:
an average value and a variance value of each of a hue of a photographed image and a chroma of the photographed image,
a covariance in a hue-chroma space of the photographed image, and
the registered dictionary data, wherein the calculated first evaluation value indicates a non-skin region image-likeliness of the photographed image;
determine the photographed image is a non-skin region image based on the calculated first evaluation value that is within a first range, wherein the non-skin region image includes a non-skin region;
generate a first output based on the determination that the photographed image is the non-skin region image;
determine, based on a difference between a first distance and a second distance, the photographed image is captured in a state in which a camera is not in contact with a skin, wherein
the first distance is between a brightness histogram of the photographed image and a brightness histogram of a first image photographed prior to the photographed image,
the first image is photographed in the state in which the camera is not in contact with the skin,
the second distance is between the brightness histogram of the photographed image and a brightness histogram of a second image photographed prior to the photographed image, and
the second image is photographed in a state in which the camera is in contact with the skin; and
generate a second output based on the determination that the photographed image is captured in the state in which the camera is not in contact with the skin.

2. The information processing apparatus according to claim 1, wherein the CPU is further configured to output a first feedback to a user based on the determination that the photographed image is the non-skin region image.

3. The information processing apparatus according to claim 2, wherein the CPU is further configured to generate a second feedback corresponding to the calculated first evaluation value.

4. The information processing apparatus according to claim 1, wherein
the CPU is further configured to output metadata to a device that analyzes the photographed image, and
the metadata indicates that the photographed image is the non-skin region image.

5. The information processing apparatus according to claim 4, wherein the CPU is further configured to output one of the calculated first evaluation value or data corresponding to the calculated first evaluation value to the device.

6. The information processing apparatus according to claim 1, wherein
the CPU is further configured to calculate the first evaluation value based on a result of a discriminant function,
the result of the discriminant function is further based on input of information on the hue of the photographed image to the discriminant function, and
the discriminant function is generated based on the registered dictionary data.

7. The information processing apparatus according to claim 1, wherein
the CPU is further configured to determine the photographed image is the non-skin region image based on a proportion of a plurality of image regions that is larger than a specific proportion,
the plurality of image regions includes a first pixel value of a third image and a second pixel value of a fourth image,
a difference between the first pixel value and the second pixel value exceeds a threshold value,
the third image is photographed based on irradiation with light beams of a first wavelength,
the fourth image is photographed based on irradiation with light beams of a second wavelength, and
the first wavelength is different from the second wavelength.

8. The information processing apparatus according to claim 1, wherein the CPU is further configured to:
determine position displacement of a photographed portion of a plurality of sequentially photographed images, and
generate a third output based on the determination of the position displacement of the photographed portion.

9. The information processing apparatus according to claim 8, wherein
the CPU is further configured to determine the position displacement of the photographed portion based on one of a distance or a degree of similarity between a luminance image of a third image and a luminance image of a fourth image,
the third image is photographed before the plurality of sequentially photographed images is photographed, and
the fourth image is photographed after the plurality of sequentially photographed images is photographed.

10. The information processing apparatus according to claim 8, wherein the CPU is further configured to determine the position displacement of the photographed portion based on a change, in sensor data, that exceeds a threshold.

11. The information processing apparatus according to claim 1, wherein the CPU is further configured to:
determine one of a blur or a shake in the photographed image; and
generate a third output based on the determination of the one of the blur or the shake in the photographed image.

12. The information processing apparatus according to claim 11, wherein the CPU is further configured to:
calculate a second evaluation value, wherein the second evaluation value indicates one of a degree of the blur or a degree of the shake in the photographed image; and
determine the one of the blur or the shake in the photographed image based on the calculated second evaluation value that is within a second range.

13. The information processing apparatus according to claim 12, wherein
the CPU is further configured to calculate the second evaluation value based on a result of a discriminant function;
the result of the discriminant function is based on input of information on a frequency obtained from the photographed image to the discriminant function, and
the discriminant function is generated based on the registered dictionary data.

14. The information processing apparatus according to claim 12, wherein
the CPU is further configured to calculate the second evaluation value based on a result of a discriminant function,
the result of the discriminant function is further based on input of a difference between luminance average values of respective blocks obtained from the photographed image to the discriminant function, and
the discriminant function is generated based on the registered dictionary data.

15. An information processing method, comprising:
registering, by a memory, dictionary data, wherein the registered dictionary data is obtained based on a learning function and a hue of a non-skin region image group;
calculating, by a processor, an evaluation value based on:
an average value and a variance value of each of a hue of a photographed image and a chroma of the photographed image,
a covariance in a hue-chroma space of the photographed image, and
the registered dictionary data, wherein the calculated evaluation value indicates a non-skin region image-likeliness of the photographed image;
determining, by the processor, the photographed image is a non-skin region image based on the calculated evaluation value that is within a range, wherein the non-skin region image includes a non-skin region;
generating, by the processor, a first output based on the determination that the photographed image is the non-skin region image;
determining, based on a difference between a first distance and a second distance, the photographed image is captured in a state in which a camera is not in contact with a skin, wherein
the first distance is between a brightness histogram of the photographed image and a brightness histogram of a first image photographed prior to the photographed image,
the first image is photographed in the state in which the camera is not in contact with the skin, the second distance is between the brightness histogram of the photographed image and a brightness histogram of a second image photographed prior to the photographed image, and the second image is photographed in a state in which the camera is in contact with the skin; and generating a second output based on the determination that the photographed image is captured in the state in which the camera is not in contact with the skin.

16. A non-transitory computer-readable medium having stored thereon computer-executable instructions that, when executed by a processor, cause the processor to execute operations, the operations comprising:

registering dictionary data in a memory, wherein the registered dictionary data is obtained based on a learning function and a hue of a non-skin region image group;

calculating an evaluation value based on:
 an average value and a variance value of each of a hue of a photographed image and a chroma of the photographed image,
 a covariance in a hue-chroma space of the photographed image, and
 the registered dictionary data, wherein the calculated evaluation value indicates a non-skin region image-likeliness of the photographed image;

determining the photographed image is a non-skin region image based on the calculated evaluation value that is within a specific range, wherein the non-skin region image includes a non-skin region;

generating a first output based on the determination that the photographed image is the non-skin region image;

determining, based on a difference between a first distance and a second distance, the photographed image is captured in a state in which a camera is not in contact with a skin, wherein the first distance is between a brightness histogram of the photographed image and a brightness histogram of a first image photographed prior to the photographed image, the first image is photographed in the state in which the camera is not in contact with the skin, the second distance is between the brightness histogram of the photographed image and a brightness histogram of a second image photographed prior to the photographed image, and the second image is photographed in a state in which the camera is in contact with the skin; and generating a second output based on the determination that the photographed image is captured in the state in which the camera is not in contact with the skin.

17. An information processing apparatus, comprising:

a central processing unit (CPU) configured to:

determine a photographed image is a non-skin region image that includes a non-skin region;

determine, based on a difference between a first distance and a second distance, the photographed image is captured in a state in which a camera is not in contact with a skin, wherein the first distance is between a brightness histogram of the photographed image and a brightness histogram of a first image photographed prior to the photographed image, the second distance is between the brightness histogram of the photographed image and a brightness histogram of a second image photographed prior to the photographed image, the first image is photographed in the state in which the camera is not in contact with the skin, and the second image is photographed in a state in which the camera is in contact with the skin;

generate a first output based on the determination that the photographed image is the non-skin region image; and generate a second output based on the determination that the photographed image is captured in the state in which the camera is not in contact with the skin.

* * * * *